(12) United States Patent
Watanabe et al.

(10) Patent No.: US 10,593,031 B2
(45) Date of Patent: Mar. 17, 2020

(54) TEXTURE EVALUATION APPARATUS, TEXTURE EVALUATION METHOD, AND COMPUTER-READABLE RECORDING MEDIUM

(71) Applicant: Ricoh Company, Ltd., Tokyo (JP)

(72) Inventors: Shuhei Watanabe, Chiba (JP); Takuroh Sone, Kanagawa (JP); Hideyuki Kihara, Kanagawa (JP); Takashi Soma, Kanagawa (JP); Akihiro Iwamatsu, Kanagawa (JP); Naoki Nakamura, Saitama (JP); Takayuki Gotoh, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 369 days.

(21) Appl. No.: 15/459,178

(22) Filed: Mar. 15, 2017

(65) Prior Publication Data
US 2017/0270655 A1    Sep. 21, 2017

(30) Foreign Application Priority Data

Mar. 16, 2016 (JP) .................................. 2016-052518
Feb. 2, 2017 (JP) .................................. 2017-017821

(51) Int. Cl.
*G06T 7/00* (2017.01)
*G01B 11/30* (2006.01)
(Continued)

(52) U.S. Cl.
CPC .......... *G06T 7/0002* (2013.01); *G01B 11/303* (2013.01); *G01N 21/57* (2013.01); *H04N 7/183* (2013.01); *H04N 9/3191* (2013.01)

(58) Field of Classification Search
CPC ...................................................... G01N 1/32
See application file for complete search history.

(56) References Cited

U.S. PATENT DOCUMENTS 3,874,799 A * 4/1975 Isaacs ................... G01J 3/0251
                                                                                 250/226
4,538,913 A * 9/1985 Anthon ................ G01B 11/306
                                                                                 250/237 G
(Continued)

FOREIGN PATENT DOCUMENTS

JP      02-033091      7/1990
JP      2007-155709    6/2007
(Continued)

OTHER PUBLICATIONS

Extended European Search Report dated May 30, 2017 in European Patent Application No. 17160631.2.

*Primary Examiner* — Pankaj Kumar
*Assistant Examiner* — Timothy R Newlin
(74) *Attorney, Agent, or Firm* — Xsensus LLP (57) ABSTRACT

A texture evaluation apparatus includes a projector, an imager, and an evaluator. The projector is configured to project a two-dimensional pattern having an edge element onto an object. The imager is configured to capture an image of a surface of the object. The evaluator is configured to calculate an amount of shape change of a virtual image of the two-dimensional pattern in the image, and evaluate texture of the object based on the amount of shape change and sensory evaluation information obtained in advance.

14 Claims, 10 Drawing Sheets

(51) Int. Cl.
  *G01N 21/57* (2006.01)
  *H04N 7/18* (2006.01)
  *H04N 9/31* (2006.01)

(56) References Cited

U.S. PATENT DOCUMENTS

| | | | |
|---|---|---|---|
| 4,717,259 A | 1/1988 | Suga | |
| 4,783,826 A * | 11/1988 | Koso | G01N 21/95607 348/130 |
| 4,938,591 A * | 7/1990 | Anderson | G03B 15/003 348/E3.021 |
| 4,942,463 A * | 7/1990 | Hopkins | H04N 5/142 348/26 |
| 5,153,444 A * | 10/1992 | Maeda | G01N 21/95607 250/559.05 |
| 5,155,558 A * | 10/1992 | Tannenbaum | G01N 21/57 348/128 |
| 5,208,766 A | 5/1993 | Chang et al. | |
| 5,383,025 A * | 1/1995 | Forrest | G01B 11/306 250/237 G |
| 5,471,307 A * | 11/1995 | Koliopoulos | G01B 11/306 356/613 |
| 5,488,478 A * | 1/1996 | Bullock | G01B 11/306 250/559.22 |
| 5,550,632 A | 8/1996 | Harata | |
| 6,144,454 A * | 11/2000 | Rupieper | G01B 21/08 118/712 |
| 2004/0228529 A1 * | 11/2004 | Jerebko | G06T 7/12 382/173 |
| 2005/0278126 A1 * | 12/2005 | Rosakis | G01L 1/24 702/42 |
| 2005/0280807 A1 * | 12/2005 | Backhauss | G01N 21/9503 356/237.2 |
| 2006/0169051 A1 * | 8/2006 | Alman | G01B 11/303 73/762 |
| 2008/0068379 A1 * | 3/2008 | Larsen | G06K 9/0014 345/427 |
| 2012/0045032 A1 * | 2/2012 | Schreiber | G01N 23/06 378/58 |
| 2012/0140060 A1 * | 6/2012 | Tsuchiya | G01N 21/95607 348/126 |
| 2012/0204614 A1 * | 8/2012 | Isei | B21C 51/00 72/12.8 |
| 2013/0098127 A1 * | 4/2013 | Isei | B21C 51/00 72/17.3 |
| 2015/0109615 A1 * | 4/2015 | Muller | G01B 11/24 356/138 |
| 2016/0054724 A1 * | 2/2016 | Oda | G05B 19/4093 700/109 |
| 2016/0102971 A1 * | 4/2016 | Isei | B21C 51/00 356/601 |

FOREIGN PATENT DOCUMENTS

| | | |
|---|---|---|
| JP | 2010-243353 | 10/2010 |
| JP | 2012-227631 | 11/2012 |

* cited by examiner

TEXTURE EVALUATION APPARATUS, TEXTURE EVALUATION METHOD, AND COMPUTER-READABLE RECORDING MEDIUM

CROSS-REFERENCE TO RELATED APPLICATIONS

The present application claims priority under 35 U.S.C. § 119 to Japanese Patent Application No. 2016-052518, filed on Mar. 16, 2016 and Japanese Patent Application No. 2017-017821, filed on Feb. 2, 2017. The contents of which are incorporated herein by reference in their entirety.

BACKGROUND OF THE INVENTION

1. Field of the Invention

The present invention relates generally to a texture evaluation apparatus, a texture evaluation method, and a computer-readable recording medium.

2. Description of the Related Art

As a factor for quality evaluation of a coated plate, an aluminum plate, a lacquerware, and the like, evaluating the texture (surface appearance) of these objects has conventionally been performed. The texture has been mainly evaluated by visual judgment by a judge.

A technique of evaluating the texture of an object using an image clarity meter has also been developed. Examples of such a technique are disclosed in Japanese Examined Patent Publication No. H2-33091 and Japanese Unexamined Patent Application Publication No. 2007-155709. Japanese Examined Patent Publication No. H2-33091 discloses a technique of numerically expressing visual luster on a surface of an object by visually inspecting a chart reflected in the sample in a condition where illumination unevenness is eliminated by arranging a frosted glass between lighting and the sample. Japanese Unexamined Patent Application Publication No. 2007-155709 discloses a technique of evaluating the image clarity by projecting a reflected image of a reference ring pattern onto an object, capturing an image of the reflected image, calculating a standard deviation of amplitudes of brightness distribution of image data, and evaluating the image clarity based on a relative value with respect to a standard deviation of a reference mirror surface.

However, visual judgment, such as the measurement method of Japanese Examined Patent Publication No. H2-33091, is disadvantageous in that judgment result can vary depending on a physical condition of a judge or due to individual difference of the judge and also in that it requires personal expenses. Meanwhile, perceived texture varies with an observation environment, such as brightness. Therefore, there is a desire for developing a technique for texture evaluation that places importance on human sensory perception but is free from fluctuations and the like. However, the technique disclosed in Japanese Unexamined Patent Application Publication No. 2007-155709 evaluates image clarity of the object based on the relative value with respect to the standard deviation, which is obtained in advance, of the reference mirror surface, and therefore cannot achieve flexible evaluation adapted to human sensory perception.

SUMMARY OF THE INVENTION

According to one aspect of the present invention, a texture evaluation apparatus includes a projector, an imager, and an evaluator. The projector is configured to project a two-dimensional pattern having an edge element onto an object. The imager is configured to capture an image of a surface of the object. The evaluator is configured to calculate an amount of shape change of a virtual image of the two-dimensional pattern in the image, and evaluate texture of the object based on the amount of shape change and sensory evaluation information obtained in advance.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An object of an embodiment is to provide a technique for evaluating the texture of an object in a way that is more close to human sensory perception and more accurately.

First Embodiment

Figure 1:
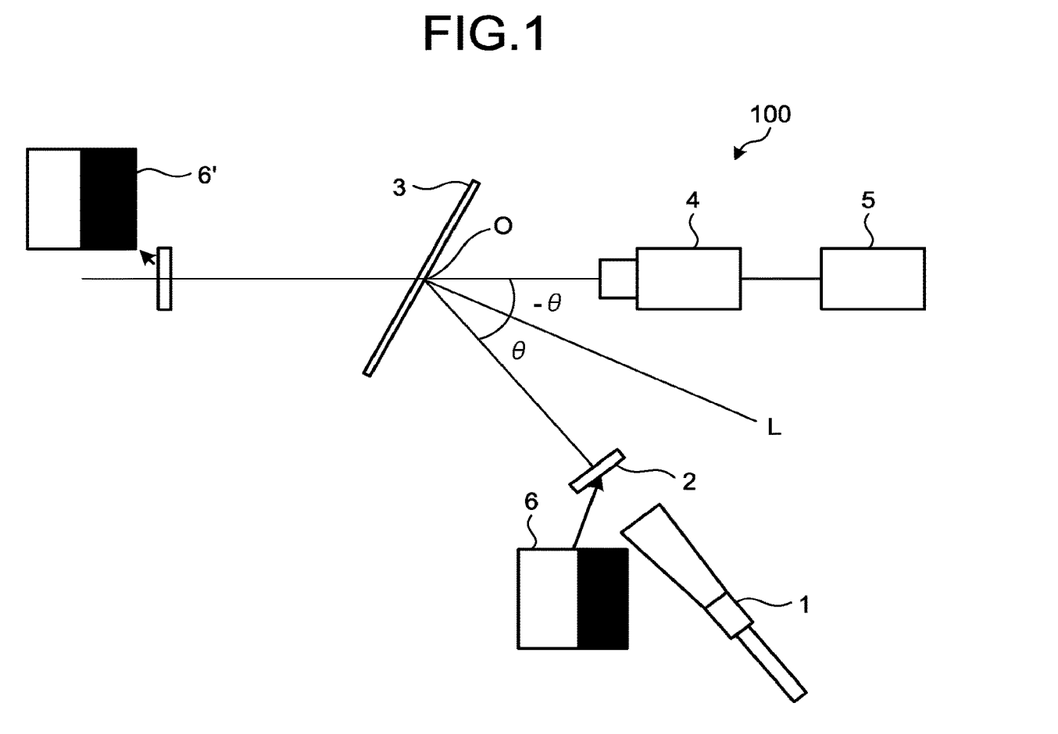
FIG. 1 is a schematic diagram illustrating an example configuration of a texture evaluation apparatus according to a first embodiment.

A texture evaluation apparatus and a texture evaluation method according to a first embodiment of the present invention are described below with reference to the accompanying drawings. FIG. 1 is a schematic diagram illustrating an example configuration of a texture evaluation apparatus 100 according to the first embodiment. As illustrated in FIG. 1, the texture evaluation apparatus 100 according to the first embodiment includes a light source 1 and a diffuser plate 2, which are an example of a projector, a sample table 3, a camera 4, which is an example of an imager, and a controller 5.

The light source 1 can be, but is not limited to, an LED (light-emitting diode) light source or the like. The light source 1 is arranged at an angle θ from the normal, which is indicated by L, to the sample table 3.

A two-dimensional pattern 6 containing an edge element is attached to the diffuser plate 2 to make an amount of shape change caused by presence/absence of texture detectable. The "containing an edge element" means having different gray levels (different shades of gray). As the two-dimensional pattern 6 containing an edge element, as illustrated in FIG. 1, a rectangular pattern of two gray levels of black and white is used. However, the two-dimensional pattern 6 is not limited to a black-and-white rectangular one, and can be any pattern, examples of which include a straight line, a curved line, a circular pattern, a grid pattern, a cruciform, and a radial pattern, so long as the pattern has different gray levels. The colors of the two-dimensional pattern 6 are not limited to black and white, and other colors can be employed.

An object O, texture of which is to be evaluated, is attached to the sample table 3. The camera 4 is arranged at an angle of −θ, which is the angle of specular reflection of light from the light source 1, from the normal L to the sample table 3.

The camera 4 captures an image of the object O onto which the two-dimensional pattern 6 is projected, thereby obtaining a two-dimensional image. In the first embodiment, a hyperspectral camera (spectral camera) is used as the camera 4. The hyperspectral camera is a camera capable of measuring luminosities on a per-light-wavelength basis and obtaining spectral distribution pixel by pixel. However, the camera 4 is not limited to a hyperspectral camera, and a digital camera, a CCD (charge-coupled device), or the like can alternatively be used.

The controller 5 includes a CPU (Central Processing Unit), a ROM (Read Only Memory), a RAM (Random Access Memory), and an HDD (Hard Disk Drive). The controller 5 controls driving of constituents, such as the light source 1 and the camera 4, of the texture evaluation apparatus 100 in accordance with program instructions for texture evaluation (hereinafter, "texture evaluation program") stored in the ROM in advance by using the RAM as a working memory. A personal computer (a desktop one or a notebook one), for example, can be used as the controller 5.

The texture evaluation program to be executed by the texture evaluation apparatus 100 of the first embodiment may be configured to be provided in a form recorded in a non-transitory computer-readable recording medium, such as a CD-ROM, a flexible disk (FD), a CD-R, or a digital versatile disk (DVD) as an installable file or an executable file.

The texture evaluation program to be executed by the texture evaluation apparatus 100 of the first embodiment may be configured to be stored in a computer connected to a network, such as the Internet, and provided by causing the program to be downloaded via the network. The texture evaluation program to be executed by the texture evaluation apparatus 100 of the first embodiment may be configured to be provided or delivered via a network, such as the Internet.

The controller 5 calculates a shape-change amount of the two-dimensional pattern 6 based on the two-dimensional image obtained by image capture by the camera 4. The controller 5 evaluates the texture of the object O based on the calculated change amount and sensory evaluation information measured in advance. Hence, the controller 5 functions also as an evaluator. "Texture" is perceived visual appearance that depends on properties of a material of the surface and means what is visually perceived from the material's properties. Examples of "texture" include "luster", "gloss", and "sharpness". In the first embodiment, "luster" of the object O is evaluated, for example.

Figure 2:
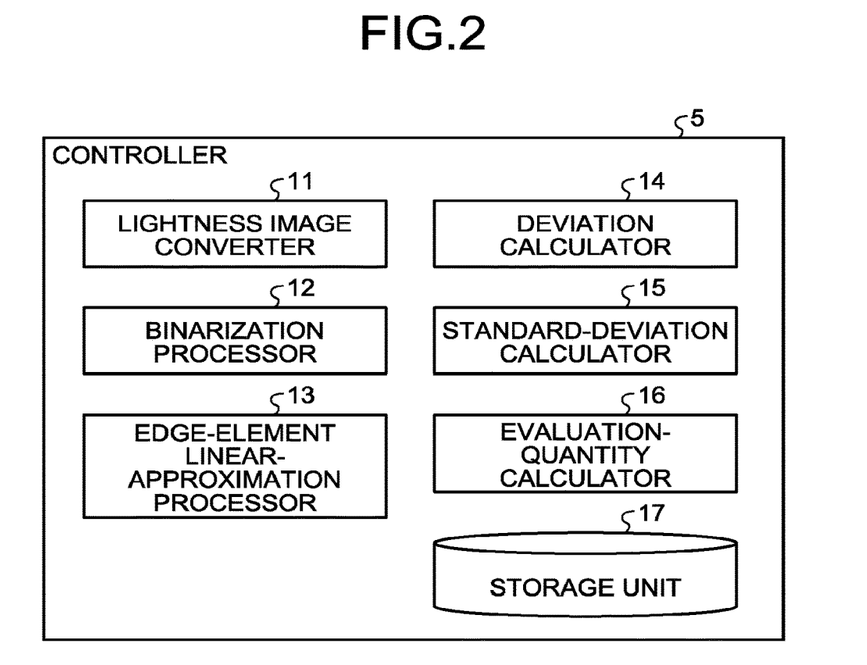
FIG. 2 is a functional block diagram of a controller illustrated in FIG. 1.

Functions of the controller 5 as an evaluator are described below with reference to the functional block diagram of FIG. 2. The CPU operates in accordance with the texture evaluation program, thereby causing the controller 5 to function as a lightness image converter 11, a binarization processor 12, an edge-element linear-approximation processor 13, a deviation calculator 14, a standard-deviation calculator 15, an evaluation-quantity calculator 16, and a storage unit 17 as illustrated in FIG. 2.

The lightness image converter 11 has a function of converting the two-dimensional image data obtained by image capture by the camera 4 into L* image data (lightness image data). The binarization processor 12 has a function of binarizing the L* image data to quantify the change amount of the two-dimensional pattern 6. The edge-element linear-approximation processor 13 has a function of calculating a straight line approximating positions, to which the edge element has been changed, based on the binarized image data. The deviation calculator 14 has a function of calculating an edge change amount (deviation) of the approximate straight line on a line-by-line basis. The standard-deviation calculator 15 calculates a standard deviation using deviations of the respective lines. The evaluation-quantity calculator 16 calculates an evaluation quantity for the texture of the object O based on the calculated standard deviation and sensory evaluation information stored in the storage unit 17. The sensory evaluation information is obtained in advance and stored in the storage unit 17.

The texture evaluation apparatus 100 according to an aspect of the present invention evaluates the texture by, in addition to measuring physical values of the object O, using a scaled set of sensory evaluation scores (subjective evaluation scores). For this reason, a subjective evaluation experiment for texture is conducted in advance. Sensory evaluation scores (subjective evaluation scores) obtained by the experiment are stored in the storage unit 17 as the sensory evaluation information.

The subjective evaluation experiment is described below. As the subjective evaluation experiment, a method generally referred to as a paired comparison method was used. The paired comparison method is a method of presenting a pair of randomly-selected objects to be evaluated to a judge and asking the judge to rate an object on the right as to whether the object has more apparent texture relative to an object on the left, for example.

To conduct the subjective evaluation experiment described above using a paired comparison method, sample objects of nine different texture types were prepared. The size of the sample objects was letter size. The judges compared a pair of presented sample objects A and B and assigned a score for texture of B with reference to texture of A as follows:

Assign +2 points if A<<B;
Assign +1 point if A<B;
Assign 0 points if A=B;
Assign −1 point if A>B; and
Assign −2 points if A>>B.

Each of the judges performed evaluation from a position away from the sample object by 500 mm in an observation environment configured so that the judge can view virtual images of a fluorescent lamp and the judge's own face reflected in the sample object. The experiment was conducted on 25 image evaluation engineers served as the judges. An evaluation score for each sample object was calculated by applying an analytical method of the quantification method III to a result of the above-described evaluation experiment.

Figure 3:
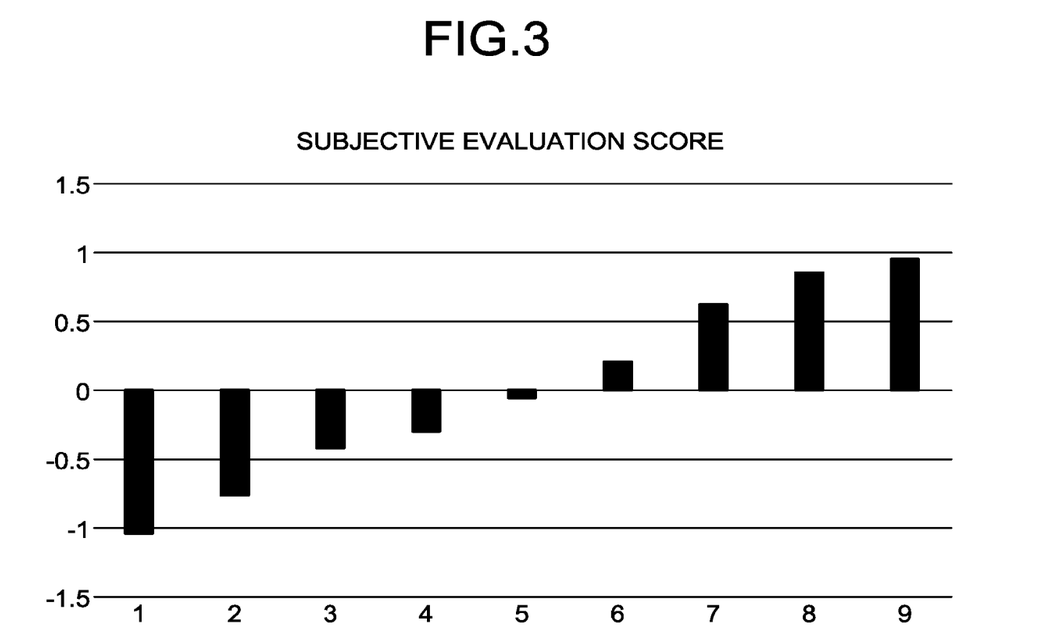
FIG. 3 is a diagram illustrating a result of a subjective evaluation experiment.

The evaluation result is presented in FIG. 3. The numbers on the horizontal axis in FIG. 3 are the numbers (consecutive numbers) assigned to the sample objects. The sample objects are arranged in the order of the subjective evaluation score. The numbers on the vertical axis indicate the subjective evaluation scores for the sample object. The smaller the value of the score, the less apparent the texture of the sample object is. Specifically, an evaluation result that the sample object "1" had poorest texture and the sample object "9" had best texture was obtained.

Referring to FIG. 3, score difference between some pair of sample objects of consecutive ranks is close. Against this backdrop, a significant test was carried out to determine whether there is a significant difference between each pair of consecutive-rank sample objects that are close in score. A result that there was no significant difference between the sample objects "2" and "4", "4" and "5", "7" and "8", and "8" and "9" was obtained.

Figure 4:
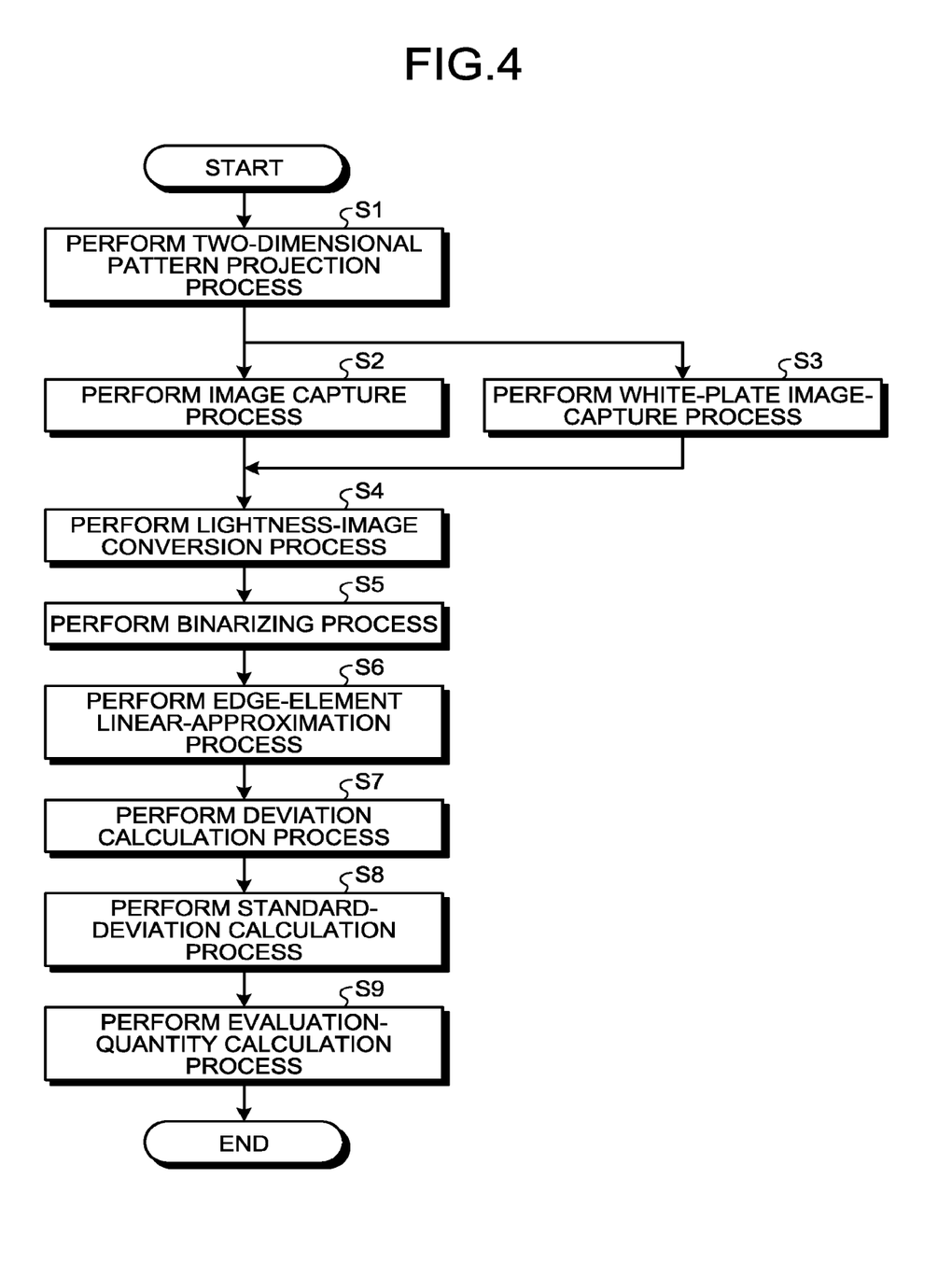
FIG. 4 is a flowchart illustrating an example procedure of a texture evaluation method according to the first embodiment.

Operations to be performed by the texture evaluation apparatus 100 of the first embodiment configured as described above to perform the texture evaluation method are described below with reference to the flowchart of FIG. 4. The object O to be evaluated is placed on the sample table 3. The texture evaluation apparatus 100 turns on the light source 1 and performs a projection process of step S1. Light emitted from the light source 1 forms an image on the diffuser plate 2 so that a virtual image 6' of the two-dimensional pattern 6 arranged on the diffuser plate 2 is projected onto the object O.

Next, at an image capture process of step S2, the texture evaluation apparatus 100 captures, using the camera 4, an image of the virtual image 6' projected onto the object O on the sample table 3 and thereby obtains two-dimensional image data. In the first embodiment, because a hyperspectral camera is used as the camera 4, spectral image data with a spectral resolution of 5 nm can be obtained as the two-dimensional image data.

At a white-plate image-capture process of step S3, the texture evaluation apparatus 100 captures, concurrently with image capture of the object O, an image of a reference white plate and thereby obtains two-dimensional image data representing the image. This process may alternatively be performed prior to texture evaluation, and the obtained two-dimensional image data may be stored in the storage unit 17.

Next, at a lightness-image conversion process of step S4, the lightness image converter 11 converts the spectral image data to lightness ($L^*$) image data of the $L^*a^*b^*$ colorimetric system for adaptation to human sensitivity. More specifically, the lightness image converter 11 converts the spectral image data representing the object O and spectral image data representing the reference white plate measured in advance into spectral-reflectance image data, and performs conversion into image data of the CIE 1931 standard colorimetric system (X, Y, Z) using the spectral-reflectance image data, spectral distribution of lighting, and a color-matching function. Thereafter, the image data of the CIE 1931 standard colorimetric system is converted into $L^*$ image data (lightness image data) using the Y tristimulus value. Conversion into the $L^*$ image data is preferable in that the converted data is more close to human vision.

The spectral distribution can be changed depending on the observation condition for the object O. For example, to calculate a texture on an assumption that the object O is observed in an office space, the lightness image converter 11 may preferably use spectral distribution of CIE standard illuminant D50. To calculate a texture on an assumption that the object O is observed outdoor in fine weather, the lightness image converter 11 may preferably use spectral distribution for CIE standard illuminant D65. By changing the spectral distribution depending on an observation condition in this manner, an evaluation value can be calculated with the observation condition taken into account. As a result, evaluation can be performed in a way that is more close to human perception.

Next, at a binarizing process of step S5, the binarization processor 12 binarizes the lightness image obtained at step S4, thereby quantifying a shape-change amount of the edge element in the two-dimensional pattern 6. In the binarizing process, the $L^*$ image data is binarized using a predetermined threshold value, so that how the two-dimensional pattern 6 is changed can be explicitly visualized (quantified).

Figure 5:
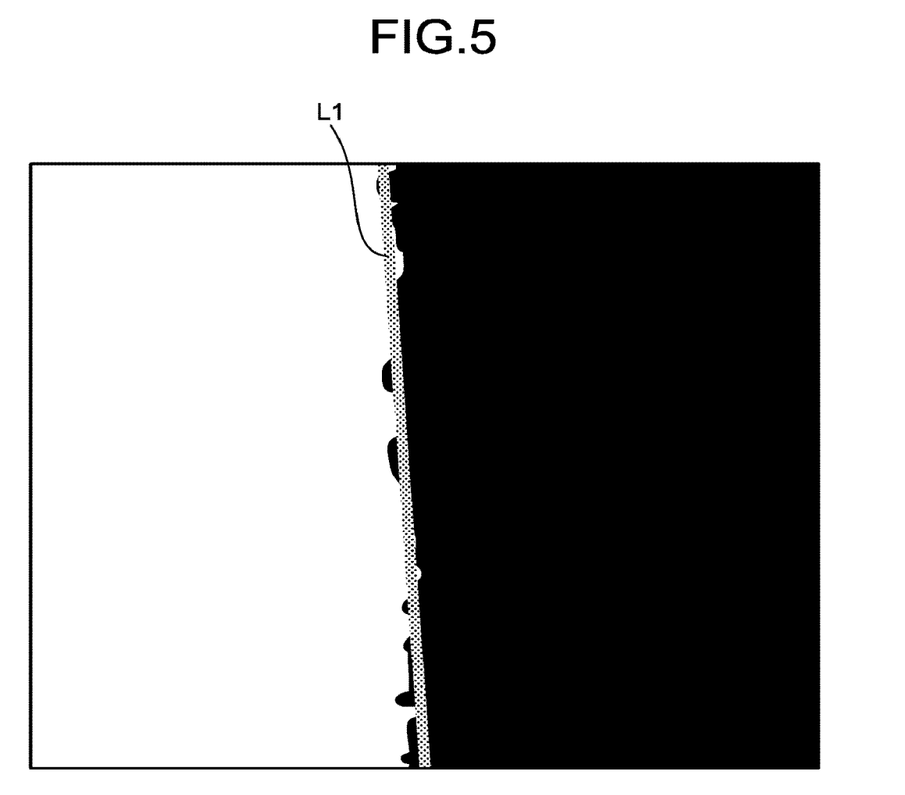
FIG. 5 is a schematic diagram illustrating an approximation straight line derived from binarized image data.

Thereafter, at an edge-element linear-approximation process of step S6, the edge-element linear-approximation processor 13 calculates a straight line that approximates the positions, to which the edge element in the image data binarized at step S5 has been changed, using the least-square method. In the schematic diagram of FIG. 5, the approximate straight line is indicated by L1. The image measured in FIG. 5 is approximately 30 mm×30 mm in size and is approximately 700 dpi (dots per inch) in resolution.

Next, at a deviation calculation process of step S7, the deviation calculator 14 calculates an amount of distortion or, put another way, an amount of edge change (deviation), of the approximate straight line calculated at step S6 on a line-by-line basis.

At a standard-deviation calculation process of step S8, the standard-deviation calculator 15 calculates a sum of squares of the deviations of the respective lines, divides the sum by the number of pixels in the image data, and takes the square root of the result. Thus, a standard deviation is obtained.

Lastly, at an evaluation-quantity calculation process of step S9, the evaluation-quantity calculator 16 obtains an evaluation equation (in the first embodiment, Evaluation equation (A) below) for calculating an evaluation quantity y from the standard deviation obtained at step S8 and the subjective evaluation scores (stored in the storage unit 17 or the like) obtained in advance. The evaluation quantity y for the texture (visual luster) of the object O is calculated using the obtained Evaluation equation (A). In Evaluation equation (A), x is the standard deviation. Evaluation equation (A) is written as a logarithmic function with the Weber-Fechner law "the intensity of a sensation is proportional to the logarithm of the intensity of the stimulus causing it" taken into account.

$$y = -1.35 \times \log x + 0.93 \qquad (A)$$

Figure 6:
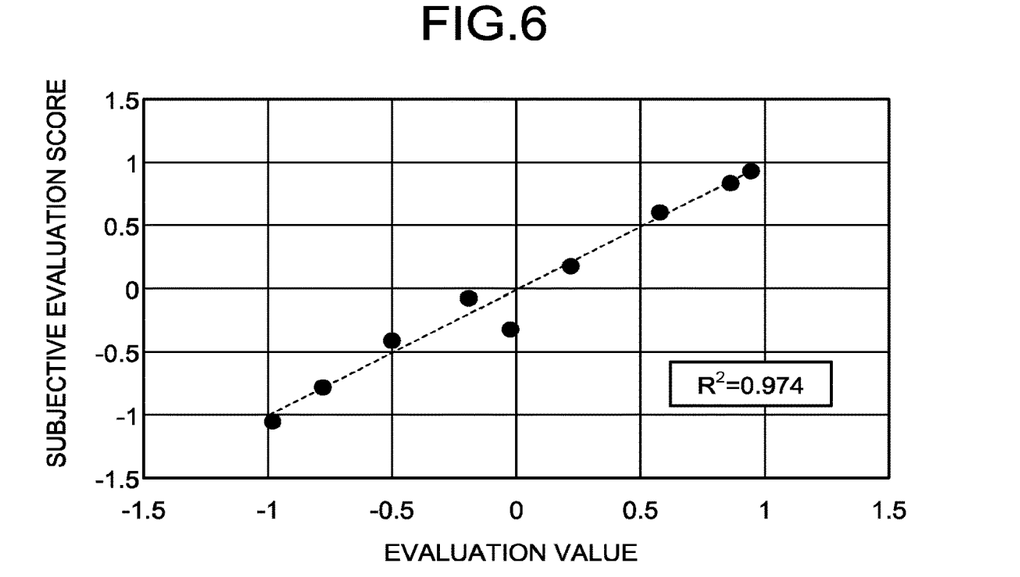
FIG. 6 is a correlation diagram between evaluation quantities calculated by the texture evaluation method of the first embodiment and subjective evaluation scores.

A correlation diagram between evaluation quantities (evaluation values) calculated by the above-described texture evaluation method and the subjective evaluation scores obtained in advance is illustrated in FIG. 6. The contribution ratio $R^2$ is 0.974, which indicates that the evaluation quantities obtained in the first embodiment are considerably close to human subjective perception. Furthermore, it is shown that reversal in the subjective evaluation rank does not occur between the objects O when there is a significant difference between the objects O.

As described above, in the first embodiment, a two-dimensional image of the object O, in which a two-dimensional pattern containing an edge element is reflected to form a virtual image of the two-dimensional pattern, is captured. A shape-change amount of the virtual image is calculated. The texture of the object O is evaluated based on the change amount and the sensory evaluation information measured in advance. Accordingly, the first embodiment can provide the texture evaluation apparatus and the texture evaluation method with which the texture of the object O can be evaluated in a way that is more close to human sensory perception, without suffering from fluctuations resulting from a physical condition and individual difference of a judge, and more accurately.

The program according to the first embodiment causes a computer to function as a storage unit (the storage unit 17) that stores the sensory evaluation scores (subjective evaluation scores) serving as the sensory evaluation information, and an evaluator (the controller 5) that performs the lightness-image conversion process, the binarizing process, the edge-element linear-approximation process, the deviation calculation process, the standard-deviation calculation process, and the evaluation-quantity calculation process, thereby evaluating the texture of the object O. Accordingly, the first embodiment can provide the program that causes a computer to perform the texture evaluation method, with which the texture of the object O can be evaluated in a way that is more close to human sensory perception, without suffering from fluctuations resulting from a physical condition and individual difference of a judge, and more accurately.

In the first embodiment, a hyperspectral camera is used; spectral image data is converted into lightness image data; and the evaluation value is calculated based on the lightness image data. Accordingly, evaluation can be performed in a manner adjusted to human color sensitivity. Furthermore, because spectral image data can be obtained, spectral distribution can be changed depending on a desired observation environment, for example.

In the first embodiment, the texture is evaluated by evaluating a change amount of distortion of the edge element in the captured virtual image 6'. Accordingly, in contrast to a conventional point measurement, an evaluation value that is highly correlated with subjective perception can be calculated based on distortion of the edge element in the two-dimensional image data.

In the first embodiment, the standard deviation is used in evaluating the change amount of distortion of the edge element in the captured virtual image 6'. However, the first embodiment is not intended to limit the method for evaluating the change amount thereto, and other method can alternatively be used.

In the first embodiment, the lightness image converter 11 performs conversion from spectral image data into lightness image data using the spectral-reflectance image data obtained by dividing the spectral image data representing the object O by the spectral image data representing the reference white plate pixel by pixel, the spectral distribution, and the color matching function. Accordingly, conversion into the spectral-reflectance image data can be performed while simultaneously correcting uneven illumination in the captured image. Furthermore, the conversion into the spectral-reflectance image data enables conversion into the L*a*b* colorimetric system. As a result, data that is more close to human vision can be obtained.

In the first embodiment, because the spectral distribution that depends on an observation condition for the object O is used, an evaluation value that takes the observation condition into account and is more adapted to human sensitivity can be calculated.

Hereafter, texture evaluation using an existing image clarity meter and that using an existing gloss meter are described below as Comparative Examples 1 and 2 with reference to the drawings.

Comparative Example 1

An image clarity meter of Comparative Example 1 is described below with reference to FIG. 7. An image clarity meter 50 of Comparative Example 1 is a device that measures the degree of image clarity of a sample object 52 in accordance with JIS K 7374. Whether texture is good or poor is to be determined based on a result of the measurement.

Figure 7:
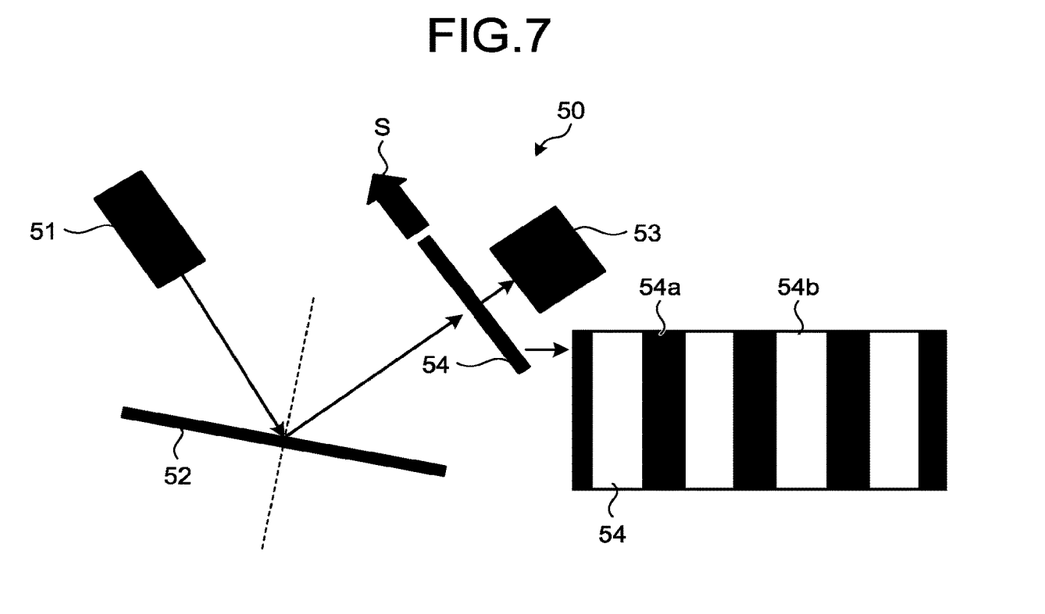
FIG. 7 is a diagram illustrating a schematic configuration of an image clarity meter of Comparative Example 1.

As illustrated in FIG. 7, the image clarity meter 50 of Comparative Example 1 causes a light source 51 to irradiate the sample object 52 with light and determines an amount of light specularly reflected from the sample object 52 using a photodetector 53. In the image clarity meter 50 of Comparative Example 1, a plate 54 is arranged between the sample object 52 and the photodetector 53. The plate 54 is formed by alternately arranging light shielding portions 54a that shield light reflected from the sample object 52 and transparent portions 54b that allow the reflected light to pass through in a comb-like fashion. The plate 54 is moved in a traveling direction S, thereby changing the amount of the reflected light incident on the photodetector 53.

Figure 8:
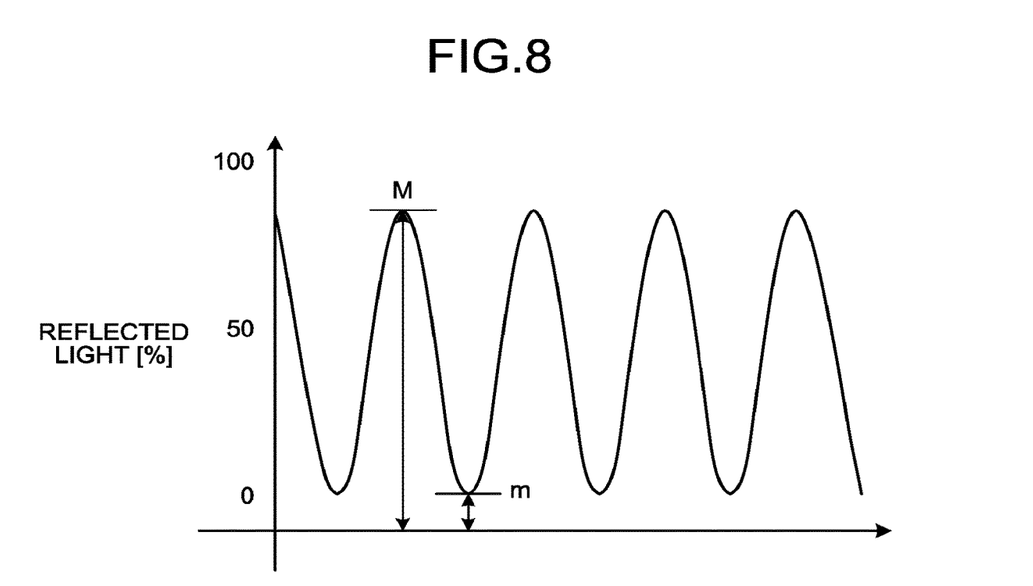
FIG. 8 is a diagram illustrating an amount of reflected light caused to vary by a plate of Comparative Example 1.

The amount of the reflected light varied using the plate 54 exhibits such a periodic form as that illustrated in FIG. 8. The image clarity meter 50 of Comparative Example 1 evaluates image clarity by applying a maximum value M and a minimum value m of the reflected light to Equation (1) below. Specifically, when the sample object 52 has good texture, because light is more specularly reflected, the value of the maximum value M is large and the value of the minimum value m is small. By contrast, when the sample object 52 has poor texture, because light is more diffused, the value of the maximum value M is small and the value of the minimum value m is large.

$$\text{Image clarity} = \frac{M-m}{M+m} \times 100 \qquad (1)$$

Figure 9:
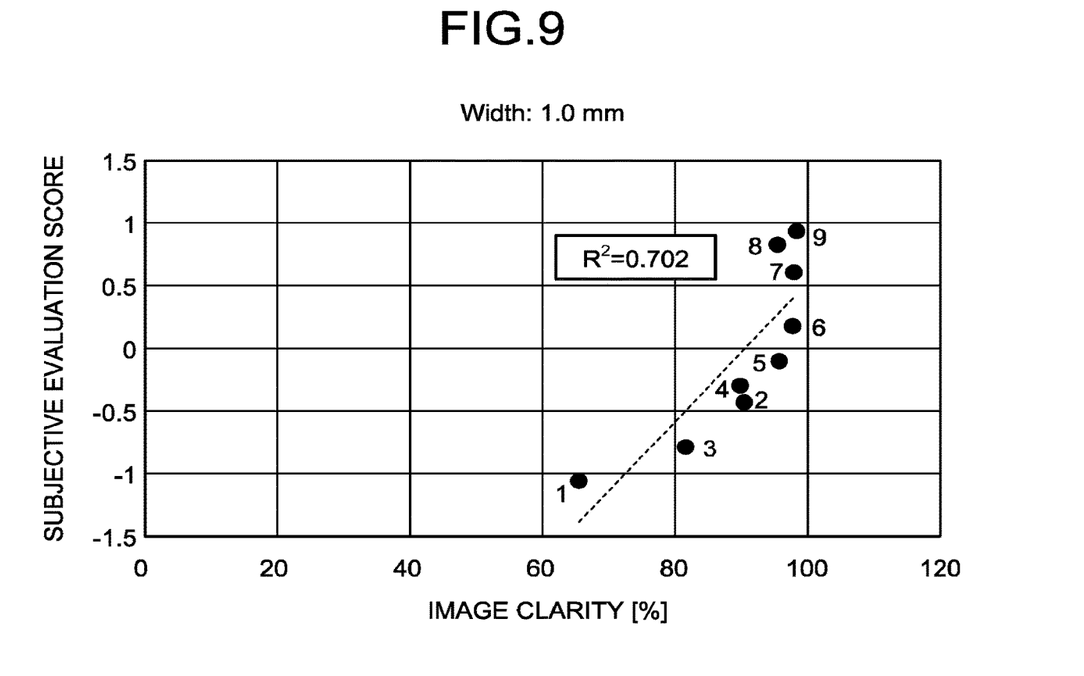
FIG. 9 is a correlation diagram between a meticulosity measurement result obtained when the width of light shielding portions and transparent portions is 1.0 mm and the subjective evaluation scores of Comparative Example 1.
Figure 10:
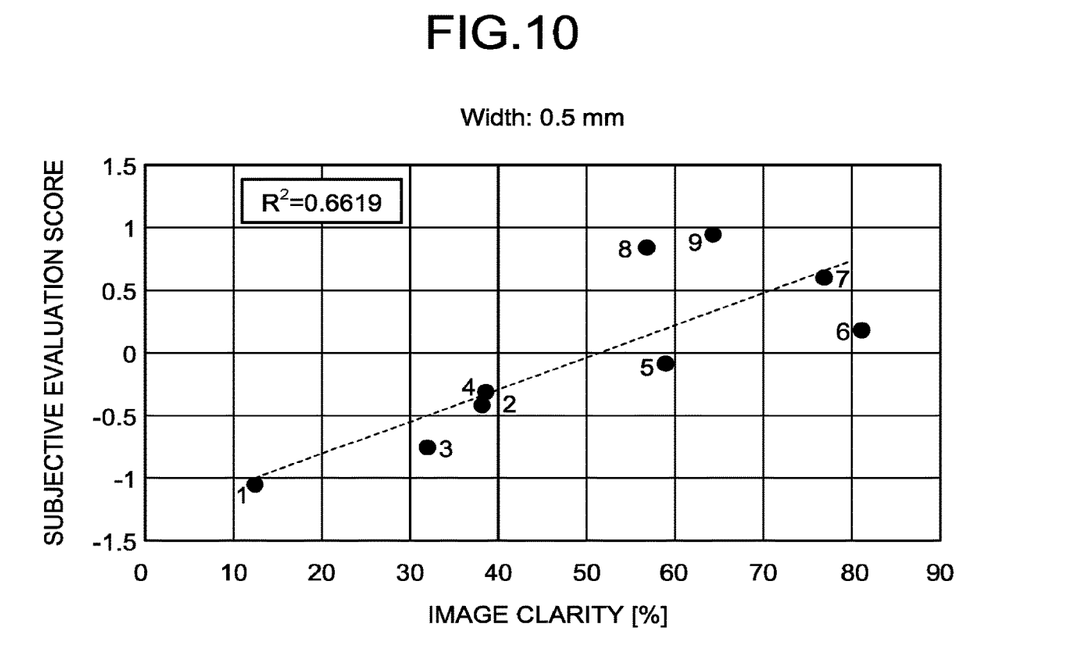
FIG. 10 is a correlation diagram between a meticulosity measurement result obtained when the width of the light shielding portions and the transparent portions is 0.5 mm and the subjective evaluation scores of Comparative Example 1.

The light shielding portions 54a and the transparent portions 54b of the plate 54 are varied in width in five levels. FIG. 9 and FIG. 10 illustrate correlation diagrams between the subjective evaluation scores and a meticulosity measurement result measured when the width of the light shielding portions 54a and the transparent portions 54b is 1.0 mm and that measured when the same is 0.5 mm, respectively. As the sample object 52, the same sample objects as the nine sample objects used in the subjective evaluation experiment of the first embodiment are used.

As illustrated in FIG. 9 and FIG. 10, a result that the contribution ratios $R^2$ are 0.702 and 0.662 (0.6619), respectively, both of which are not low, are obtained. However, the ranks of the sample objects "5" to "9" do not match the result of the subjective evaluation. Accordingly, in spite that the contribution ratios are high, it will be difficult to assume these as correct evaluation. The reason therefor can be ascribed to that only contrast is calculated by performing one-dimensional measurement, and an undesirable result, such as reversal of measured values or that no difference exists, can be obtained from sample objects that differ only slightly in terms of luster.

Comparative Example 2

Figure 11:
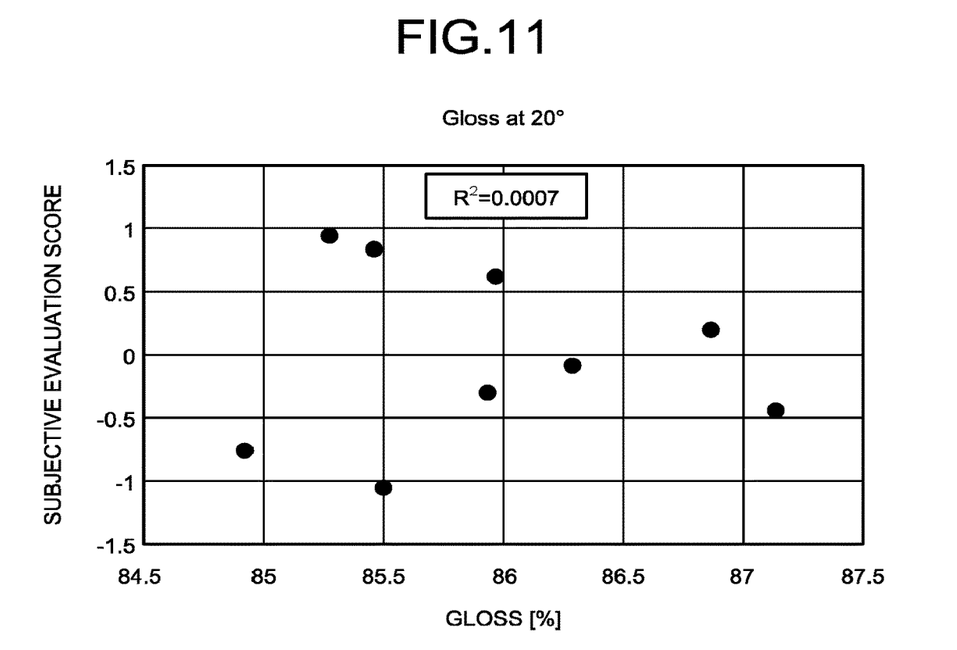
FIG. 11 is a correlation diagram between a gloss measurement result obtained using a glossmeter and the subjective evaluation scores of Comparative Example 1.

As Comparative Example 2, a glossmeter that measures the gloss of a sample object in accordance with JIS Z 8741 is used, and whether the texture is good or poor is determined based on a measurement result. A correlation diagram between a result of measuring gloss at 20 degrees using a glossmeter and the subjective evaluation scores is illustrated in FIG. 11. The gloss at 20 degrees is a gloss measured with each of the light source 51 and the photodetector 53 arranged at 20 degrees from the normal to the sample object 52.

As illustrated in FIG. 11, a result that the contribution ratio $R^2$ is 0.001 (0.0007) and therefore has substantially no correlation with the subjective evaluation scores is obtained. This is presumably because difference in texture is undetectable from information about only the intensity of reflectance that is measured one-dimensionally at an average reflectance (point).

The results of the first embodiment, Comparative Example 1, and Comparative Example 2 indicate that the texture evaluation apparatus 100 and the texture evaluation method according to an aspect of the present invention can evaluate the texture of an object in a way that is more close to human sensory perception and more accurately than conventional techniques.

Second Embodiment

A second embodiment is described below. Elements of the second embodiment identical to those of the first embodiment are denoted by like reference numerals and repeated description is omitted.

The second embodiment is configured to evaluate the texture of an object as follows. An image of the object, in which a two-dimensional pattern is reflected to form a virtual image, is captured. Frequency characteristics of the shape of the virtual image are calculated from a shape-change amount of the virtual image. The texture of the object is evaluated based on the frequency characteristics and the sensory evaluation information.

Figure 12:
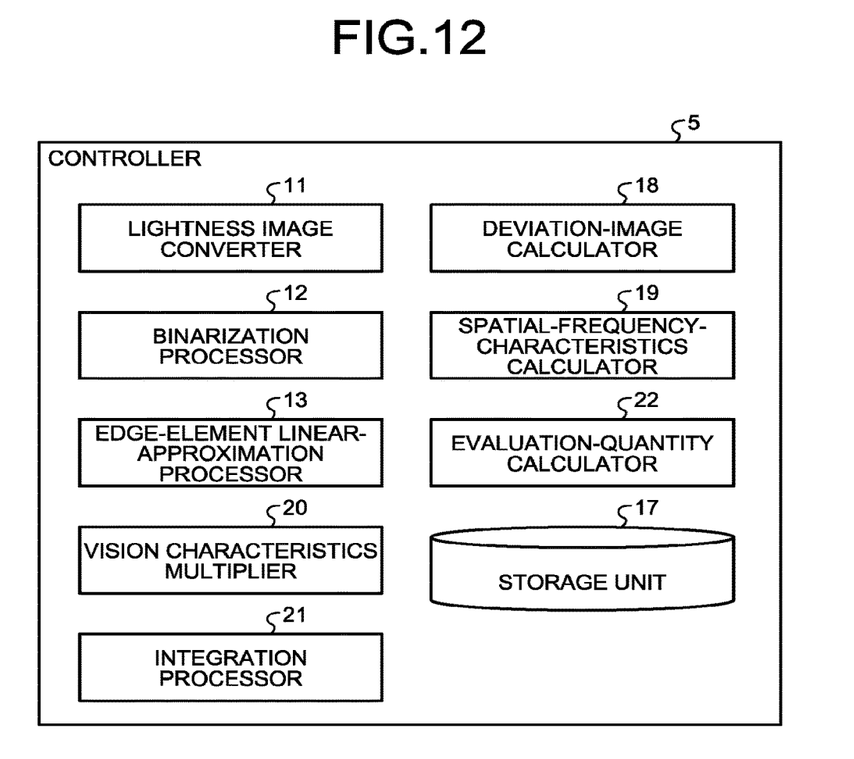
FIG. 12 is a functional block diagram of a controller of a texture evaluation apparatus according to a second embodiment.

FIG. 12 is a functional block diagram of a controller according to the second embodiment. As illustrated in FIG. 12, the CPU operates in accordance with a texture evaluation program, thereby causing the controller 5 to function as the lightness image converter 11, the binarization processor 12, the edge-element linear-approximation processor 13, a deviation-image calculator 18, a spatial-frequency-characteristics calculator 19, a vision characteristics multiplier 20, an integration processor 21, an evaluation-quantity calculator 22, and the storage unit 17. The lightness image converter 11, the binarization processor 12, the edge-element linear-approximation processor 13, and the storage unit 17 are similar to those of the above-described first embodiment, and repeated description is omitted.

The deviation-image calculator 18 calculates an edge change amount (deviation image) of the approximate straight line obtained by the edge-element linear-approximation processor 13 on a line-by-line basis.

The spatial-frequency-characteristics calculator 19 performs Fourier transform on the deviation image obtained by the deviation-image calculator 18, thereby calculating frequency characteristics of an edge-changed portion.

The vision characteristics multiplier 20 assigns a weight to the frequency characteristics obtained by the spatial-frequency-characteristics calculator 19 using a visual transfer function (VTF) for use in expressing human vision characteristics.

The visual transfer function (VTF) is described below. The visual transfer function (VTF) is spatial frequency characteristics of human vision system. The visual transfer function (VTF) is assigned as a weight to the spatial frequency characteristics of the edge-changed portion by multiplying the spatial frequency characteristics by the VTF. Frequency characteristics that are adjusted for human visual sensitivity at the observation distance of the subjective evaluation can thus be calculated. Accordingly, the texture can be evaluated based on the frequency characteristics adjusted for the distance at which the object surface is observed by the judge. As a result, an evaluation value having a higher contribution ratio to subjective evaluation can be obtained. There are a number of reports about the visual transfer function (VTF). Among them, the visual transfer function (VTF) used in lightness fluctuations by Dooley, etc. is well known.

Figure 13:
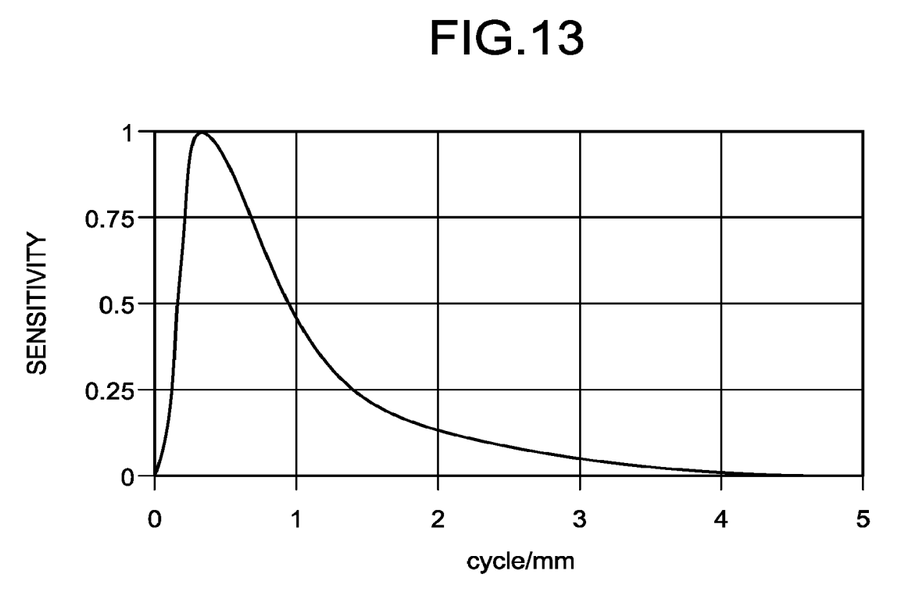
FIG. 13 is a diagram illustrating a visual transfer function (VTF) in a subjective evaluation experiment.

FIG. 13 is a diagram illustrating a visual transfer function (VTF) in a subjective evaluation experiment. FIG. 13 illustrates a visual transfer function (VTF) for an observation distance of 500 mm in the subjective evaluation experiment. Referring to FIG. 13, the sensitivity peaks at or near approximately 0.3 cycle/mm and approaches 0 from or near 4 cycles/mm.

The integration processor 21 calculates the integral of the frequency characteristics weighted by the vision characteristics multiplier 20.

The evaluation-quantity calculator 22 calculates evaluation quantities for the texture of the object O based on the integrals of the respective samples calculated by the integration processor 21 and the subjective evaluation scores stored in the storage unit 17.

Figure 14:
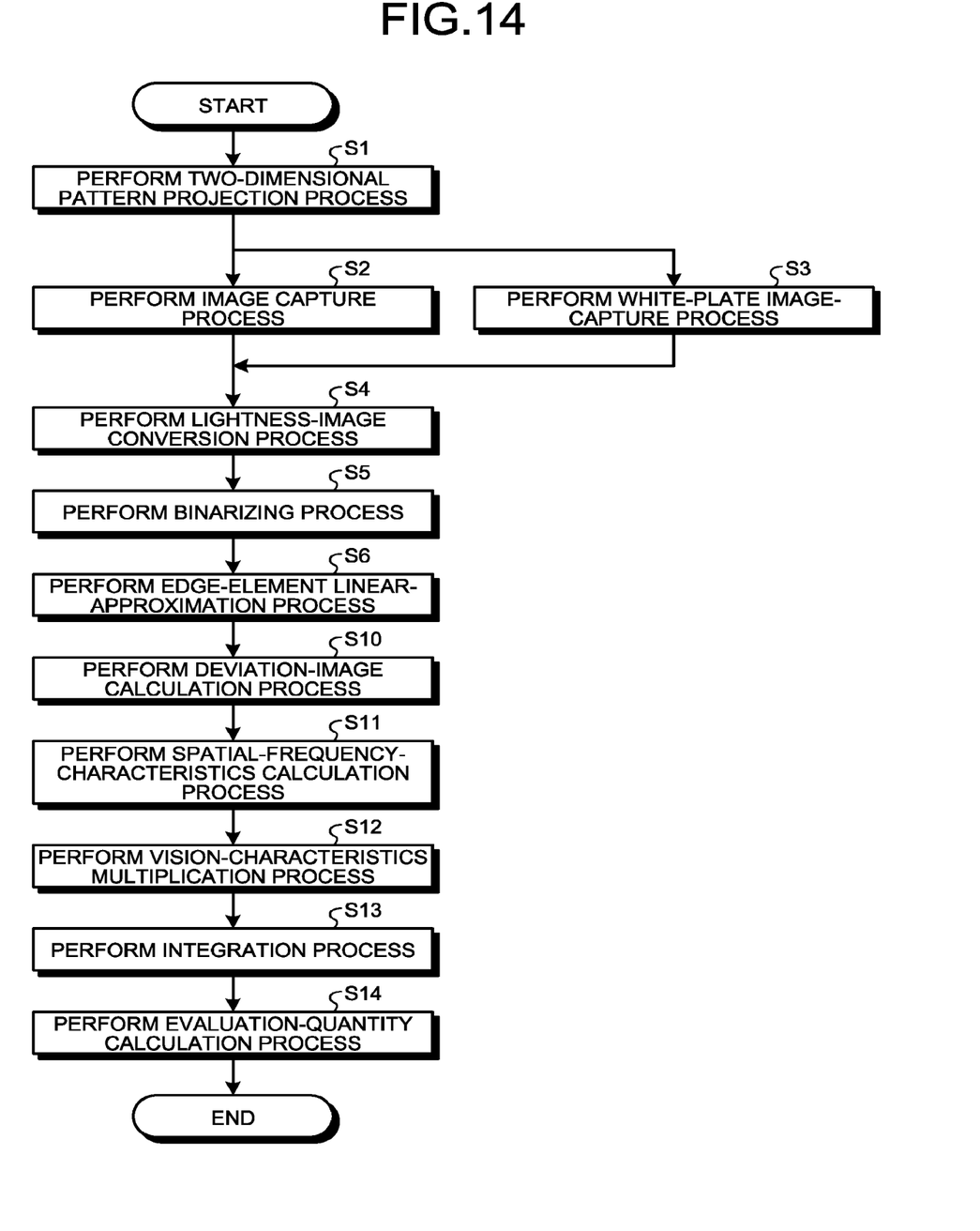
FIG. 14 is a flowchart illustrating an example procedure of a texture evaluation method according to the second embodiment.

Operations to be performed by the texture evaluation apparatus 100 of the second embodiment configured as described above to perform the texture evaluation method are described below with reference to the flowchart of FIG. 14. Processing of steps S1 to S6 of FIG. 14 is identical to processing of steps S1 to S6 described with reference to FIG. 4, and repeated description is omitted.

Next, at a deviation-image calculation process of step S10, the deviation-image calculator 18 calculates an edge change amount (deviation image) of the approximate straight line calculated at step S6 on a line-by-line basis.

Next, at a spatial-frequency-characteristics calculation process of step S11, the spatial-frequency-characteristics calculator 19 performs Fourier transform on the deviation image obtained at step S10, thereby calculating frequency characteristics of the edge-changed portion.

Next, at a vision-characteristics multiplication process of step S12, the vision characteristics multiplier 20 assigns a weight to the frequency characteristics obtained at S11 using a visual transfer function (VTF) for use in expressing human vision characteristics.

Next, at an integration process of step S13, the integration processor 21 calculates the integral of the frequency characteristics weighted at step S12.

Lastly, at an evaluation-quantity calculation process of step S14, the evaluation-quantity calculator 22 obtains an evaluation equation (in the second embodiment, Evaluation equation (B) below) for calculating the evaluation quantity y from the integral of each of the samples (the object O) calculated at step S13 and the subjective evaluation scores stored in the storage unit 17. The evaluation quantity y for the texture (visual luster) of the object O is calculated using the obtained Evaluation equation (B). In Evaluation equation (B), x is the standard deviation. Evaluation equation (B) is written as a logarithmic function with the Weber-Fechner law "the intensity of a sensation is proportional to the logarithm of the intensity of the stimulus causing it" taken into account.

$$y = -1.49 \times \log x + 9.81 \quad (B)$$

Figure 15:
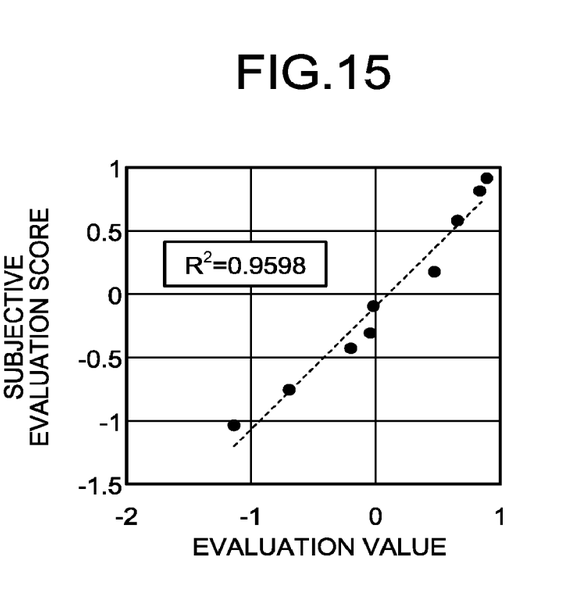
FIG. 15 is a correlation diagram between evaluation quantities calculated by the texture evaluation method of the second embodiment and the subjective evaluation scores.

A correlation diagram between subjective evaluation quantities (evaluation values) calculated by the above-described texture evaluation method and the subjective evaluation scores obtained in advance is illustrated in FIG. 15. The contribution ratio $R^2$ is 0.9598, which indicates that the evaluation quantities obtained in the second embodiment are considerably close to human subjective perception. Furthermore, it is shown that reversal in the subjective evaluation rank does not occur between the objects O when there is a significant difference between the objects O.

As described above, in the second embodiment, a two-dimensional image of the object O, in which a two-dimensional pattern containing an edge element is reflected to form a virtual image, is captured. Frequency characteristics of the shape of the virtual image are calculated. The texture of the object O is evaluated based on the frequency characteristics of the shape of the virtual image that are weighted with human vision characteristics. Accordingly, the second embodiment can provide the texture evaluation apparatus and the texture evaluation method with which texture of the object O can be evaluated in a manner that is more close to human sensory perception, without suffering from fluctuations due to a physical condition and individual difference of a judge, and more accurately.

According to an aspect of the present invention, it is possible to evaluate the texture of an object in a way that is more close to human sensory perception and more accurately.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, nonvolatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. A texture evaluation apparatus, comprising:
   a projector configured to project a two-dimensional pattern having an edge element onto an object;
   an imager configured to capture an image of a surface of the object, the captured image including a virtual image of the two-dimensional pattern including the edge element; and
   processing circuitry configured to
      determine, using image data of the captured image, a reference line approximating the edge element in the captured image,
      calculate, as an amount of shape change, a measure of positional deviation of the edge element in the captured image from the determined reference line, and
      evaluate a texture of the object based on the calculated amount of shape change and predetermined sensory evaluation information.

2. The texture evaluation apparatus according to claim 1, wherein the processing circuitry is further configured to calculate frequency characteristics of a shape of the virtual image from the amount of shape change, and evaluate the texture of the object based on the calculated frequency characteristics and the predetermined sensory evaluation information.

3. The texture evaluation apparatus according to claim 2, wherein the processing circuitry is further configured to assign a weight to the frequency characteristics using a visual transfer function used in expressing human vision characteristics.

4. The texture evaluation apparatus according to claim 1, wherein
the imager is a spectral camera, and
the processing circuitry is further configured to perform conversion of spectral image data obtained by capturing an image of the object with the spectral camera into lightness image data, and evaluate the texture of the object based on the lightness image data.

5. The texture evaluation apparatus according to claim 1, wherein the processing circuitry is further configured to evaluate distortion of the edge element in the virtual image in the image captured with the imager to evaluate the texture of the object.

6. The texture evaluation apparatus according to claim 4, wherein the processing circuitry is further configured to use spectral-reflectance image data obtained by dividing the spectral image data representing the object by a spectral image of a reference white plate pixel by pixel, a spectral distribution, and a color matching function to perform the conversion from the spectral image data into the lightness image data.

7. The texture evaluation apparatus according to claim 6, wherein the processing circuitry is further configured to use, as the spectral distribution, a particular spectral distribution that depends on an observation condition for the object.

8. The texture evaluation apparatus of claim 1, wherein the processing circuitry is further configured to determine the reference line by calculating, using a least-squares method, a straight line that approximates positions of the edge element in the captured image.

9. The texture evaluation apparatus of claim 8, wherein the processing circuitry is further configured to calculate the amount of shape change by calculating deviations of the positions of the edge element from the straight line.

10. The texture evaluation apparatus of claim 1, wherein the processing circuitry is further configured to evaluate the texture, which is one of luster, gloss, and sharpness.

11. A texture evaluation method, comprising:
projecting a two-dimensional pattern having an edge element onto an object;
capturing an image of a surface of the object, the captured image including a virtual image of two-dimensional pattern including the edge element;
determining, using image data of the captured image, a reference line approximating the edge element in the captured image,
calculating, as an amount of shape change, a measure of positional deviation of the edge element in the captured image from the determined reference line; and
evaluating a texture of the object based on the calculated amount of shape change and predetermined sensory evaluation information.

12. The texture evaluation method according to claim 11, wherein
the calculating step includes calculating frequency characteristics of a shape of the virtual image from the amount of shape change, and
the evaluating step includes evaluating the texture of the object based on the calculated frequency characteristics and the predetermined sensory evaluation information.

13. A non-transitory computer-readable recording medium with an executable program stored thereon, wherein the program, when executed by a computer that includes a memory to store sensory evaluation information, instructs the computer to perform a method comprising:
obtaining an image of an object onto which a two-dimensional pattern having an edge element is projected, the obtained image including a virtual image of the two-dimensional pattern including the edge element;
determining, using image data of the obtained image, a reference line approximating the edge element in the obtained image,
calculating, as an amount of shape change, a measure of positional deviation of the edge element in the obtained image from the determined reference line; and
evaluating a texture of the object based on the calculated amount of shape change and the sensory evaluation information.

14. The computer-readable recording medium according to claim 13, wherein
the calculating step includes calculating frequency characteristics of a shape of the virtual image from the amount of shape change, and
the evaluating step includes evaluating the texture of the object based on the calculated frequency characteristics and the sensory evaluation information.

* * * * *